United States Patent
Goldstein

(10) Patent No.: US 11,266,533 B2
(45) Date of Patent: *Mar. 8, 2022

(54) OCCLUSION DEVICE CAPABLE OF OCCLUDING AN EAR CANAL

(71) Applicant: Staton Techiya, LLC, Delray Beach, FL (US)

(72) Inventor: Steven W. Goldstein, Delray Beach, FL (US)

(73) Assignee: Staton Techiya, LLC, Delray Beach, FL (US)

( * ) Notice: Subject to any disclaimer, the term of this patent is extended or adjusted under 35 U.S.C. 154(b) by 644 days.

This patent is subject to a terminal disclaimer.

(21) Appl. No.: 16/207,858

(22) Filed: Dec. 3, 2018

(65) Prior Publication Data

US 2019/0142641 A1 May 16, 2019

Related U.S. Application Data

(63) Continuation of application No. 14/633,201, filed as application No. PCT/US2012/053640 on Sep. 4, 2012, now Pat. No. 10,143,592.

(51) Int. Cl.
*A61F 11/10* (2006.01)
*A61F 11/08* (2006.01)
*A61B 5/12* (2006.01)
*A61F 11/12* (2006.01)

(52) U.S. Cl.
CPC ............. *A61F 11/10* (2013.01); *A61B 5/125* (2013.01); *A61F 11/08* (2013.01); *A61F 11/12* (2013.01)

(58) Field of Classification Search
CPC .. H04R 1/1008; H04R 1/1016; H04R 25/652; H04R 1/1058; H04R 25/658; H04R 25/604; H04R 25/654; A61F 11/14; A61F 11/08; A61F 11/10; A61F 11/008
See application file for complete search history.

(56) References Cited

U.S. PATENT DOCUMENTS

| 7,756,281 | B2 | 7/2010 | Goldstein et al. |
| 8,047,207 | B2 | 11/2011 | Perez et al. |
| 8,194,864 | B2 | 6/2012 | Goldstein et al. |
| 8,199,919 | B2 | 6/2012 | Goldstein et al. |
| 8,208,644 | B2 | 6/2012 | Goldstein et al. |

(Continued)

FOREIGN PATENT DOCUMENTS

WO 2011163565 12/2011

OTHER PUBLICATIONS

World Intellectual Property Office, "PCT International Search Report and Written Opinion," for International Application No. PCT/US2012/053640, dated Nov. 20, 2012, document of 10 pages.

*Primary Examiner* — Ophelia A Hawthorne
(74) *Attorney, Agent, or Firm* — Akerman LLP; Peter A. Chiabotti

(57) ABSTRACT

Occlusion devices, earpiece devices and methods of occluding an ear canal are provided. An occlusion device includes an insertion element, a foldable element and an expandable element. The foldable element is disposed on the insertion element and is configured to receive a medium via the insertion element. The expandable element is disposed over the foldable element. The foldable element is configured to unfold, responsive to the medium, and cause the expandable element to expand to contact the ear canal.

19 Claims, 12 Drawing Sheets

(56) References Cited

U.S. PATENT DOCUMENTS

| | | |
|---|---|---|
| 8,208,652 B2 | 6/2012 | Keady |
| 8,221,861 B2 | 7/2012 | Keady |
| 8,229,128 B2 | 7/2012 | Keady |
| 8,251,925 B2 | 8/2012 | Keady et al. |
| 8,312,960 B2 | 11/2012 | Keady |
| 8,437,492 B2 | 5/2013 | Goldstein et al. |
| 8,550,206 B2 | 10/2013 | Keady et al. |
| 8,554,350 B2 | 10/2013 | Keady et al. |
| 8,600,067 B2 | 12/2013 | Usher et al. |
| 8,631,801 B2 | 1/2014 | Keady |
| 8,657,064 B2 | 2/2014 | Staab et al. |
| 8,678,011 B2 | 3/2014 | Goldstein et al. |
| 8,718,313 B2 | 5/2014 | Keady |
| 8,848,939 B2 | 9/2014 | Keady et al. |
| 8,917,880 B2 | 12/2014 | Goldstein et al. |
| 8,992,710 B2 | 3/2015 | Keady |
| 9,113,267 B2 | 8/2015 | Usher et al. |
| 9,123,323 B2 | 9/2015 | Keady |
| 9,138,353 B2 | 9/2015 | Keady |
| 9,185,481 B2 | 11/2015 | Goldstein et al. |
| 9,216,237 B2 | 12/2015 | Keady |
| 9,539,147 B2 | 1/2017 | Keady et al. |
| 9,757,069 B2 | 9/2017 | Keady et al. |
| 9,781,530 B2 | 10/2017 | Usher et al. |
| 9,843,854 B2 | 12/2017 | Keady |
| 10,012,529 B2 | 7/2018 | Goldstein et al. |
| 10,143,592 B2 * | 12/2018 | Goldstein ............... A61F 11/10 |
| 10,190,904 B2 | 1/2019 | Goldstein et al. |
| 2009/0071486 A1 | 3/2009 | Perez et al. |
| 2009/0071487 A1 | 3/2009 | Keady |
| 2009/0214072 A1 | 8/2009 | Staab et al. |
| 2010/0241256 A1 | 9/2010 | Goldstein et al. |
| 2011/0163565 A1 | 12/2011 | Goldstein et al. |
| 2013/0098706 A1 | 4/2013 | Keady |
| 2013/0149192 A1 | 6/2013 | Keady |
| 2014/0003644 A1 | 1/2014 | Keady et al. |
| 2014/0026665 A1 | 1/2014 | Keady |
| 2014/0373854 A1 | 12/2014 | Keady |
| 2016/0015568 A1 | 1/2016 | Keady |
| 2016/0192077 A1 | 6/2016 | Keady |
| 2016/0295311 A1 | 10/2016 | Keady et al. |
| 2017/0134865 A1 | 5/2017 | Goldstein et al. |
| 2018/0054668 A1 | 2/2018 | Keady |
| 2018/0132048 A1 | 5/2018 | Usher et al. |
| 2018/0220239 A1 | 8/2018 | Keady et al. |
| 2019/0082272 A9 | 3/2019 | Goldstein et al. |

* cited by examiner

OCCLUSION DEVICE CAPABLE OF OCCLUDING AN EAR CANAL

CROSS-REFERENCE TO RELATED APPLICATION(S)

This application is a continuation of and claims priority to U.S. patent application Ser. No. 14/633,201, filed on Sep. 15, 2015, now U.S. Pat. No. 10,143,592, which is a National Stage Entry of PCT/US 2012/053640, filed on Sep. 4, 2012, each of which are herein incorporated by reference in their entireties.

FIELD OF THE INVENTION

The present invention relates to occlusion devices such as earpiece devices which are capable of adjustably occluding an ear canal to provide, for example, selective and/or variable degrees of sound attenuation.

BACKGROUND OF THE INVENTION

People may be exposed to noise pollution from their ambient environment (for example, from traffic, from construction sites, from aircraft, etc.). People may also be intentionally exposed to high sound levels (for example, from cell phones, MP3 players, home theater equipment, rock concerts, etc.). Studies have shown that ear damage, which may lead to permanent hearing impairment, is not only increasing in the general population, but may be increasing at a significantly faster rate in younger populations.

The potential for hearing damage may be a function of both a level and a duration of exposure to a sound stimulus. Studies have also indicated that hearing damage is a cumulative phenomenon. Although hearing damage due to industrial or background noise exposure is more thoroughly understood, there may also be a risk of hearing damage from the exposure to intentional excessive noise, such as with the use of headphones.

Devices which attenuate sound directly to the ear canal are known. Conventional devices typically fit in the ear, around the ear and/or beyond the ear. Examples of these devices include headphones, headsets, earbuds and hearing aids. Earpieces that occlude the ear canal may provide increased attenuation of the ambient environment, offering improved sound isolation. However, conventional in-ear earpieces may be fitted for a cross-section of a population. Conventional in-ear earpieces, thus, may not be properly fitted to the individual user and may not be adequately sealed, leading to reduced sound attenuation of the ambient environment.

Despite significant advances in recent years, there is still a recognized need for improved adaptable earpiece devices which are capable of providing effective sound attenuation to a broad spectrum of users, despite significant variation in their ear canal dimensions and configurations, and which can be readily adjusted or tuned once in the ear to adapt to different acoustic environments.

SUMMARY OF THE INVENTION

One aspect of the invention provides an occlusion device configured to be capable of occluding an ear canal. The occlusion device includes an insertion element, a foldable element and an expandable element. The foldable element is disposed on the insertion element and is configured to receive a medium via the insertion element. The expandable element is disposed over the foldable element. The foldable element is configured to unfold, responsive to the medium, and cause the expandable element to expand to contact the ear canal.

Another aspect of the invention provides a method of occluding an ear canal. The method includes placing an occlusion device within the ear canal. The occlusion device includes an insertion element, a foldable element disposed on the insertion element and an expandable element disposed over the folded element. The foldable element is configured to receive a medium via the insertion element in a space between the insertion element and the foldable element. The method also includes introducing the medium into the space between the insertion element and the foldable element, causing the folded element to unfold and causing the expandable element to expand to contact the ear canal.

BRIEF DESCRIPTION OF THE DRAWINGS

The invention may be understood from the following detailed description when read in connection with the accompanying drawings. It is emphasized that, in accordance with common practice, various features of the drawings may not be to scale. On the contrary, the dimensions of the various features may be arbitrarily expanded or reduced for clarity. Moreover, in the drawings, common numerical references are used to represent like features. Included in the drawings are the following figures.

DETAILED DESCRIPTION OF THE INVENTION

The following description of exemplary embodiment(s) is merely illustrative in nature and is in no way intended to limit the invention, its application, or uses.

Exemplary embodiments are directed to or can be operatively used on various wired or wireless earpiece devices. For example, the earpiece devices can be without transducers (e.g., for a noise attenuation application) or can be with one or more transducers (e.g., an ambient sound microphone (ASM), an ear canal microphone (ECM), an ear canal receiver (ECR) (i.e., a loudspeaker)) for monitoring/providing sound. In all of the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undue experimentation, to determine the materials needed given the enabling disclosure herein.

Figure 1:
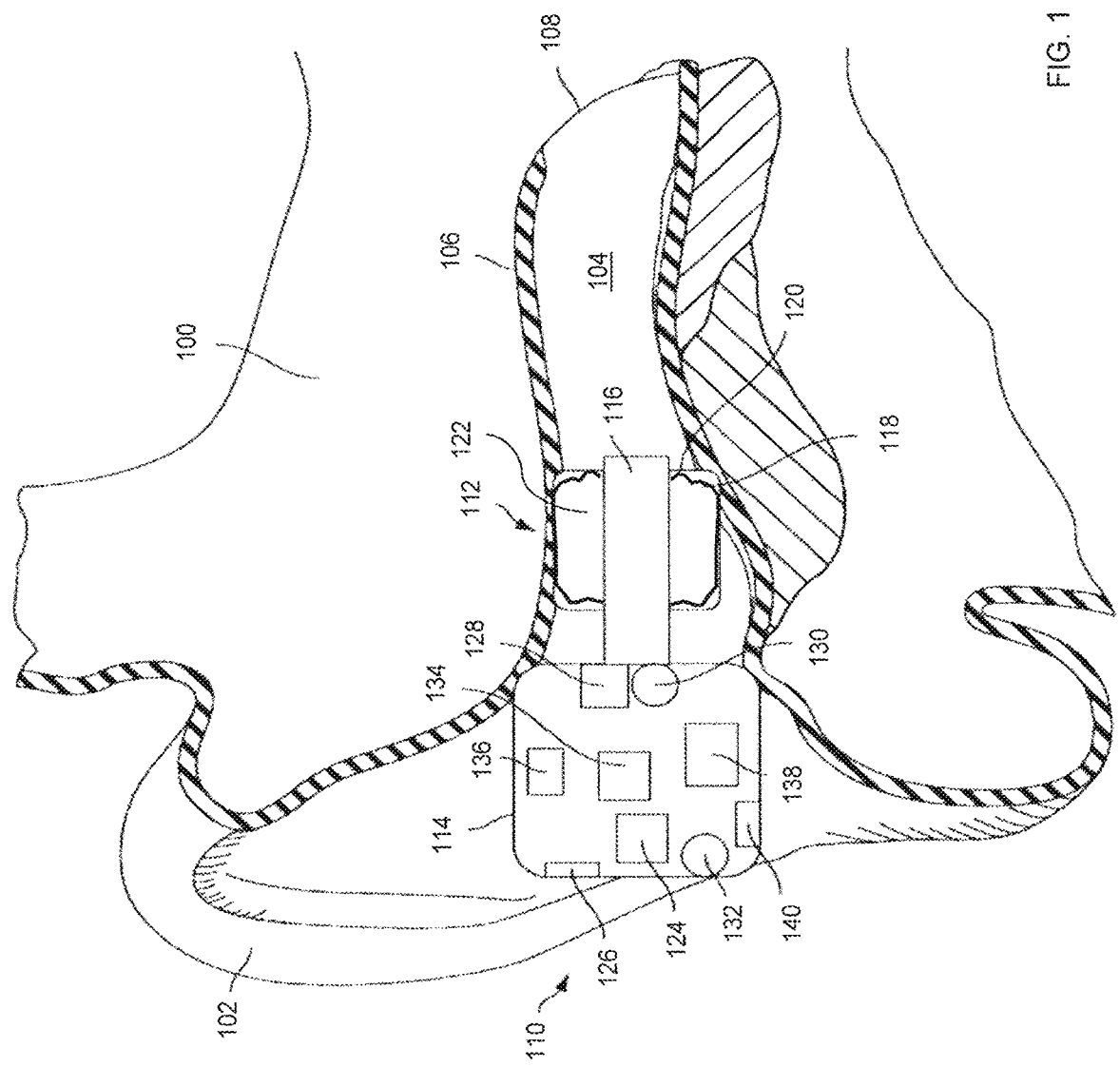
FIG. 1 is a cross section diagram of an exemplary earpiece device inserted in an ear canal, according to an embodiment of the present invention.

Referring to FIG. 1, a cross section diagram of an exemplary earpiece device 110 is shown. Earpiece device 110 is shown relative to a general physiology of ear 100. An external portion of ear 100 includes pinna 102. An internal portion of ear 100 includes ear canal 104 and tympanic membrane 108.

Pinna 102 is a cartilaginous region of ear 100 that focuses acoustic information from an ambient environment to ear canal 104. Wall 106 (also referred to herein as ear canal wall 106) of ear canal 104 forms an acoustic chamber, which terminates with tympanic membrane 108. Sound enters ear canal 104 and is subsequently received by tympanic membrane 108. Tympanic membrane 108 is a flexible membrane in the middle ear that couples to components of the inner ear. In general, acoustic information resident in ear canal 104 vibrates tympanic membrane 108. The vibration is converted to a signal (corresponding to the acoustic information) that is provided to an auditory nerve (not shown).

In general, ear canal 104 may vary substantially in shape and size over the human population. Although not illustrated in FIG. 1, ear canal 104 is generally not straight or regularly shaped. Because the volume, shape, and length of ear canal 104 may substantially vary, there has been difficulty in providing a system that may effectively seal ear 100, attenuate noise, mitigate the occlusion effect, operate under different environmental conditions, and fit a majority of the population.

For example, hearing aid manufacturers typically generate a full custom earpiece for individuals that includes a mold of the patient's ear canal. The ear canal mold is then used to form a hearing aid housing. The procedure to create an ear canal mold is costly, cumbersome, and is not easily adaptable for high volume production. In contrast to conventional earpieces, earpiece device 110 may be configured to be adaptable to a broad spectrum of users while being capable of providing effective sound attenuation, as described further below.

Figure 2:
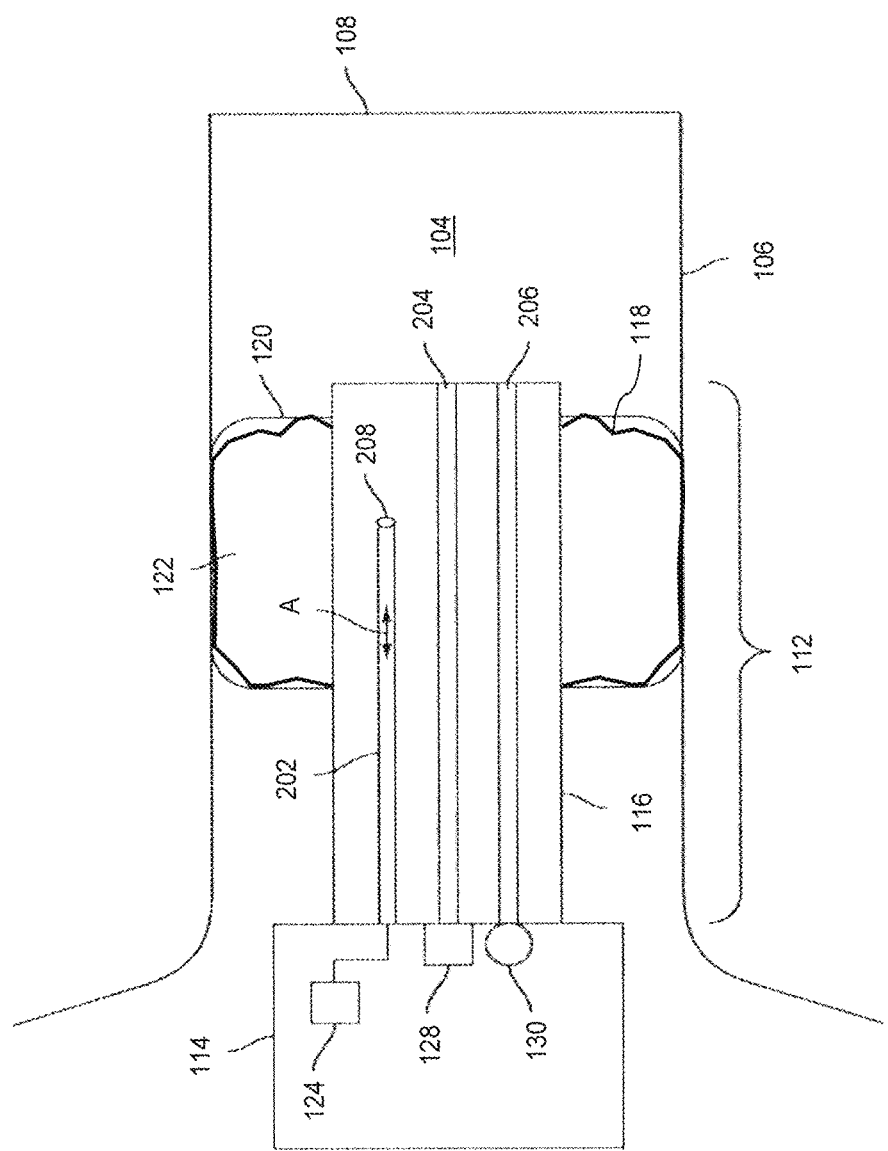
FIG. 2 is a cross section diagram of a portion of the earpiece device shown in FIG. 1, according to an embodiment of the present invention.

Earpiece device 110 may include occlusion section 112 and housing unit 114 coupled to occlusion section 112. Occlusion section 112 may be configured to be inserted in ear canal 104, at a location between the entrance to the ear canal 104 and tympanic membrane 108. Housing unit 114 may be positioned outside of ear canal 104. In FIG. 2, housing unit 114 is illustrated as being disposed in ear 100. It is understood that housing unit 114 may also be configured to be placed behind ear 100 or may be placed partially behind ear 100 and partially in ear 100. Occlusion section 112 may be permanently coupled to housing unit 114 or may be configured to be disposably coupled to housing unit 114.

Occlusion section 112 may include insertion element 116, foldable element 118 and expandable element 120. Insertion element 116 may be coupled to foldable element and expandable element 120 and may be used to position expandable element 120 in ear canal 104. Expandable element 120 is configured to be expanded, via foldable element 112 and medium 122, as described further below with respect to FIGS. 3A-3C. In general, expandable element 120 may be configured to form an acoustic seal with a portion of ear canal wall 106. Expandable element 120 may be configured to partially or fully occlude ear canal 104, to provide various degrees of acoustic isolation (i.e., attenuation of one or more frequencies of ambient sound) at tympanic membrane 108. In one embodiment, expandable element 120 is a non-foamed (solid) film or membrane. In another embodiment, expandable element 120 is a foam material, which may serve to provide a more comfortable fit for the user once expandable element 120 has been expanded to an extent effective to bring it into contact with ear canal wall 106. In yet another embodiment, expandable element 120 comprises a plurality of layers, including an inner non-foam layer and an outer foam layer for contact with ear canal wall 106.

In operation, expandable element 120 may be inserted in ear canal 104 in a contracted state (or in a partially contracted state). After insertion, expandable element 120 may be subsequently expanded (e.g., by way of introduction of medium 122 capable of causing foldable element 118 to unfold), such that expandable element 120 conforms to ear canal 104 and forms at least a partial acoustic seal with ear canal 104. To remove earpiece device 110, expandable element 120 may be contracted (e.g., by removing at least part of medium 122 causing foldable element 118 to fold) back to the contracted state (or a partially contracted state). Accordingly, earpiece device 110 may then be easily removed from ear canal 104.

Although expandable element 120 is illustrated as being of an annular-disc shape, it is understood that expandable element 120 may be formed of other shapes, such as conical-shaped, or toroidal-shaped. Although FIG. 1 illustrates a single expandable element 120, it is understood that occlusion section 112 may include more than one expandable element 120, where a respective foldable element 118 of each expandable element 120 may be filled with a same medium 122 or with different mediums 122.

Although FIG. 1 illustrates a single foldable element 118, occlusion section 112 may include multiple foldable elements 118. For example, two or more foldable elements may be arranged along a length of insertion element 116 and filled with medium 122 (or different mediums 122) in order to unfold and expand expandable element 120. According to another example, two or more foldable elements may be co-located on insertion element 116 (such as an inner foldable element in an outer foldable element, where each foldable element 118 may be filled with a same or different mediums 122).

Housing unit 114 may include inflation management system 124 for controlling the transfer of medium 122 to and from occlusion section 112, for expanding and contracting expandable element 120. Housing unit 114 may also include user interface 126 coupled to inflation management system 124. Inflation management system 124 may be activated responsive to user interface 126, in order to unfold and fold foldable element 1118, thereby respectively expanding and contracting expandable element 120. Housing unit 114 may also include further electrical components. Inflation management system 124 may include any suitable system capable of transferring medium 122 to and from expandable element 120. For example, inflation management system 124 may include a pump actuator and a valve housing (not shown).

According to one embodiment, earpiece device 110 may include inflation management system 124 and user interface 126, without any electro-acoustical elements. In this example embodiment, earpiece device 110 may be configured simply as a sound isolation device, with a predetermined sound attenuation characteristic selected according to the physical parameters of occlusion section 112.

According to another embodiment, housing unit 114 may include electrical components as well as one or more electro-acoustical components. For example, housing unit 114 may include ear canal receiver (ECR) 128 (i.e., a loudspeaker), controller 134, memory 136, battery 138 and communication unit 140.

ECR 128, memory 136, communication unit 140, user interface 126 and inflation management system 124 may be controlled by controller 134. Controller 134 may include, for example, a logic circuit, a digital signal processor or a microprocessor.

Communication unit 140 may be configured to receive and/or transmit signals to earpiece device 110. Communication unit 140 may be configured for wired and/or wireless communication with an external device (e.g., an MPEG player or a mobile phone).

Battery 138 may power the electrical and electro-acoustical components in housing unit 114. Battery 138 may include a rechargeable or replaceable battery.

The acoustic seal provided by occlusion section 112 may significantly reduce a sound pressure level at tympanic membrane 108 from an ambient sound field at the entrance to ear canal 104 (to provide sound isolation). For example, occlusion section 112 having a high pass filter characteristic may substantially attenuate lower frequencies. Because of the sound isolation of occlusion section 112, ECR 128 may generate a full range bass response time when reproducing sound in earpiece device 110.

According to another embodiment, housing unit 114 may include an ear canal microphone (ECM) 130 located adjacent to ECR 128, which may also be acoustically coupled to ear canal 104. ECM 130 may be configured to measure a sound pressure level in ear canal 104. The sound pressure level in ear canal 104 may be used, for example, to test the hearing acuity of a user, to confirm an integrity of the acoustic seal, and/or to confirm the operation of ECM 130 and ECR 128.

According to another embodiment, housing unit 114 may include at least one ambient sound microphone (ASM) 132, as well as ECM 130 and ECR 128. ASM 132 may be configured to monitor a sound pressure of the ambient environment at the entrance to ear 100. In at least one exemplary embodiment, earpiece device 110 may actively monitor a sound pressure level both inside and outside ear canal 104 and may enhance spatial and timbral sound quality, while maintaining supervision to ensure safe sound reproduction levels. Earpiece device 110, in various embodiments may conduct listening tests, filter sounds in the environment, monitor sounds in the environment, present notification based on the monitored sounds, maintain constant audio content to ambient sound levels, and/or filter sound in accordance with a personalized hearing level.

Earpiece device 110 may be configured to generate an ear canal transfer function (ECTF) to model ear canal 104 (via ECR 128 and ECM 130), as well as an outer ear canal transfer function (OETF) (via ASM 132). Earpiece device 110 may be configured to determine a sealing profile with ear 100 to compensate for any acoustic leakage. Earpiece device 110 may be configured to monitor a sound exposure to ear canal 104 (for example, from ECR 128 as well as from ambient noise measured via ASM 132).

Referring to FIG. 2, a cross section diagram of earpiece device 110 is shown, which illustrates further components of insertion element 116. In FIG. 2, only some of the components of housing unit 114 are shown, for convenience. According to an exemplary embodiment, insertion element 116 may include pneumatic channel 202. Pneumatic channel 202 may be coupled to foldable element 118 and to inflation management system 124. Pneumatic channel 202 may be used to transfer medium 122 (illustrated by double headed arrow A) to and from foldable element 118 via at least one port 208.

According to an exemplary embodiment, expandable element 120 may be expanded by medium 122 flow into a space between an inner surface of foldable element 118 and an outer surface of insertion element 116. That is, the flow of medium 122 into this space unfolds the foldable element 118, causing it to come into contact with the inner surface of the expandable element 120 and push it radially outward towards the inner surface of the ear canal wall 106.

In at least one exemplary embodiment, insertion element 116 may include at least one acoustic channel (e.g., acoustic channel 204 and/or acoustic channel 206) for receiving or delivering audio content. For example, housing unit 114 may include ECR 128. Insertion element 116 may, thus, include acoustic channel 204 for delivering sound from ECR 128 to ear canal 104. As another example, housing unit 114 may include ECR 128 and ECM 130. In this example, insertion element 116 may include acoustic channels 204, 206, respectively coupled to ECR 128 and ECM 130. Acoustic channel 206 may deliver sound from ear canal 104 to ECM 130.

As described above, expandable element 120 may form an acoustic seal with ear canal wall 106 at a location between the entrance to ear canal 104 and tympanic membrane 108. The acoustic seal by foldable element 118 and expandable element 120 may substantially attenuate sound in ear canal 104 from the ambient environment (thus providing sound isolation to ear canal 104). Insertion element 116 may also include one or more acoustic channels (e.g., acoustic channel 204 and/or acoustic channel 206) for acoustically coupling sound between ear canal 104 and one or more respective transducers (e.g., ECR 128 and/or ECM 130). Accordingly, sound transmitted to and/or from ear canal 104 via acoustic channel 204 (and/or acoustic channel 206) may be substantially isolated from the ambient environment.

As shown in FIG. 2, occlusion section 112 includes insertion element 116, a foldable element 118 and expandable element 120 attached to insertion element 116. Expandable element 120 is disposed over foldable element 118. That is, foldable element 118 is contained within expandable element 120. Both the foldable element 118 and the expandable element 120 may extend completely around the insertion element 116, in a layered arrangement, whereby the foldable element 118 forms an inner layer and the expandable element 120 forms an outer layer. In one embodiment, the expandable element 120 is arranged so that, when the occlusion section 112 is in an unexpanded state (i.e., little or no medium 122 is present between the foldable element 118 and the insertion element 116), it fits snugly over the foldable element 118. For example, the expandable element 120 in this state presses the foldable element 118 in a folded (collapsed) state against the outer surface of the insertion element 116. The overall diameter of the occlusion section 112 is thereby minimized, allowing this portion of the earpiece device 110 to be readily inserted into or removed from the ear canal 104.

As will be explained in more detail subsequently, foldable element 118 may constructed of a material that is stiffer and less compliant than the material used to fabricate expandable element 120. Thus, in one embodiment of the invention, foldable element is "non-compliant" and expandable element is "compliant" or "semi-compliant," with such terms having the same meanings as conventionally used in the medical balloon art. When little or no medium 122 is present in the space between the outer surface of insertion element 116 and the inner surface of foldable element 118, the foldable element 118 may adopt a folded configuration. However, introducing medium 122 into this space causes foldable element 118 to begin to unfold. As foldable element 118 unfolds in response to such medium 122 introduction, it pushes out against the expandable element 120 causing the expandable element 120 to stretch and expand. In one embodiment of the invention, the surface area of foldable element 118 is selected such that the expandable element 120 expands and initially contacts the inner surface of the ear canal 104 before the foldable element 118 is completely unfolded. Introduction of still further quantities of the medium 122 into the space between the outer surface of insertion element 116 and the inner surface of foldable element 118 leads to further unfolding of the foldable element 118 and exertion of greater pressure against the expandable element 120, causing a larger area of the outer surface of the expandable element 120 to come into contact with the ear canal inner surface. As will be subsequently explained in more detail, adjusting the amount of medium 122 present in this space allows the acoustic characteristics of the occlusion section 112 to be varied and adjusted as may be desired.

The dimensions and configuration of the foldable element 118 may be selected such that when it is completely unfolded and not subjected to any restrictive forces it defines a diameter that is greater than the diameter of the ear canal 104 within which the occlusion section 112 is positioned.

In one embodiment of the invention, the foldable element 118 when fully unfolded in the absence of the expandable element 120 defines a volume V1 between the inner surface of the foldable element 118 and the outer surface of the insertion element 116, the expandable element 120 when expanded to the minimum extent necessary to bring the outer periphery of the expandable element 120 into contact with an ear canal 104 defines a volume V2 between the inner surface of the expandable element 120 and the outer surface of the insertion element 116, and V1 is greater than V2. For example, V1 may be at least 10%, 20%, 30%, 40%, 50%, 60%, 70%, 80%, 90%, or 100% greater than V2 or even higher.

Figure 3C:
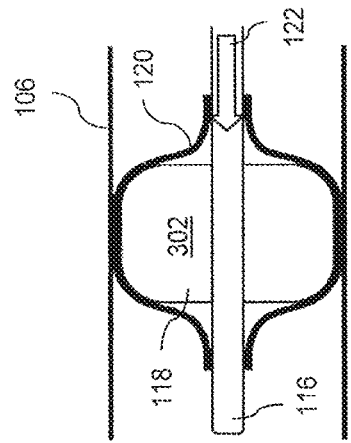
FIGS. 3A, 3B and 3C are cross section diagrams of an occlusion section of the earpiece device shown in FIG. 1, illustrating expansion of the occlusion section, according to an embodiment of the present invention.
Figure 3B:
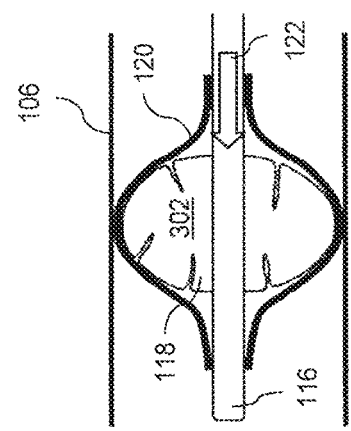
Figure 3A:
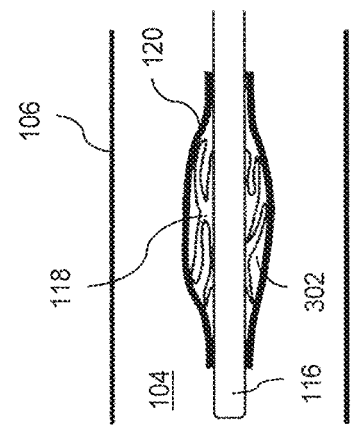

The operation of the occlusion section 112 at different stages of inflation (expansion) may be explained with the aid of the series of schematic cross-sectional representations of the occlusion section 112 illustrated in FIGS. 3A-3C.

Initially (FIG. 3A), with little or no unfolding of foldable element 118, expandable element 120 lies snugly around foldable element 118 holding it in a highly folded state against the outer surface of insertion element 116. Occlusion section 112 is positioned within ear canal 104 defined by inner wall 106. In this configuration, the ear canal 104 is not blocked, so the sound attenuation is essentially minimal.

As a medium 122 is introduced through openings (not shown) in insertion element 116 into the space between the outer insertion element surface and the inner surface of foldable element 118, foldable element 118 begins to unfold. This unfolding, caused by filling of space 302 by the medium 122, results in inflation of the foldable element 118. Inflation of the foldable element 118 in turn pushes outwardly against expandable element 120, causing expandable element 120 to elongate (stretch) and expand towards ear canal wall 106. When a sufficient quantity of medium 122 has been so introduced, ear canal 104 may be blocked by occlusion section 112 as illustrated in FIG. 3B. When the outer periphery of expandable element 120 initially contacts ear canal wall 106 so as to form a seal around the entire circumference of occlusion section 112, as shown in FIG. 3B, foldable element 118 has not yet completely unfolded. Foldable element 118 is not being stretched and there are no restoring forces set up to counter the difference in pressure between inside and the ambient. Expandable element 120 is instead being stretched (elongated) and providing the counterbalance forces. Thus, the acoustic attenuation achieved will be largely determined by the properties of the expandable element material alone.

As additional quantities of the medium 122 are introduced in the space 302 between insertion element 116 and foldable element 118, foldable element 118 further unfolds as shown in FIG. 3C. Under such conditions, foldable element 118 reaches or exceeds its critical volume. The mechanical forces counterbalancing the pressure difference are due to both the foldable element material and the expandable element material. However, when the Young's modulus (stiffness) of the foldable element material is greater than that of the expandable element material, the properties of the foldable element material will dominate. Therefore, the acoustic attenuation will be determined primarily by the characteristics of the foldable element material. The transmission loss attained will be substantially similar to what would be observed if only the foldable element 118 was present.

Accordingly, the amount of medium 122 present between insertion element 116 and foldable element 118 (which affects the extent to which foldable element 118 is inflated) can be readily varied to adjust the transmission loss provided by the occlusion section 112. The versatility of the occlusion section 112 thus is enhanced as compared to a device which relies on only one type of inflatable or expandable balloon.

The foldable element 118 may be constructed of a material selected to be relatively stiff and non-compliant, as compared to the material selected for use in fabricating the expandable element 120. In one embodiment of the invention, one or both of the foldable element material and the expandable element material are polymeric in character. That is, the materials contain at least one polymer (e.g., a high molecular weight plastic or elastomer), but may additionally contain one or more further additives typically employed in the polymer art such as fillers, plasticizers, anti-oxidants, stabilizers, impact modifiers, colorants and the like. According to one aspect of the invention, the polymer used in one or both of the foldable element 118 and the expandable element 120 is thermoplastic, although crosslinked and/or thermoset polymers may also be utilized. In one embodiment of the invention, one or both of the foldable element 118 and the expandable element 120 are relatively thin sheets or films. For example, the expandable element 120, in unstretched form, may have a thickness of from about 0.1 to about 0.5 mm and the foldable element 118 may have a thickness of from about 0.05 to about 2 mil (about 1 to about 50 microns). Generally speaking, it will be advantageous for the foldable element to be relatively thin, provided sufficient burst or tear strength is maintained, so that the foldable element is capable of collapsing and adopting a comparatively small diameter to permit the facile insertion and removal of the device. The foldable element 118 may be selected to be sufficiently thin, strong and flexible to allow it to be repeatedly folded and unfolded without tearing or otherwise losing its structural integrity and its ability to retain the medium 122 which is used to fill the space between the insertion element 116 and the foldable element 118, causing the foldable element 118 to unfold. These characteristics also permit the foldable element 118 to be tightly compressed and held against the insertion element 116 by the expandable element 120 when the medium 122 is drained from the aforementioned space, thereby allowing the diameter of the occlusion section 112 to be minimized (facilitating insertion of the occlusion section 112 into an ear canal 104 as well as its removal therefrom). Foldable element 118 may be provided with one or more pleats, which are configured to facilitate the folding of the foldable element in an ordered or preselected manner when medium 122 is removed and the foldable element collapses.

According to one embodiment of the invention, the material used for the foldable element 118 exhibits little or no elongation at break under ambient use temperatures (e.g., about 20° C. to about 40° C., for example 25° C.). For example, the foldable element material may have an elongation at break of not more than 50%, not more than 40%, not more than 30%, not more than 20%, or not more than 10%. Elongation at break may be measured by ASTM D 412.

In other aspects of the invention, the expandable element material may exhibit an elongation at break which is greater than that of the foldable element material. For example, the expandable element material may have an elongation at break of at least 200%, at least 300%, at least 400%, at least 500%, or even higher. Typically, the expandable element is fabricated from a material having an elongation at break of from about 500 to about 1500%.

In other embodiments of the invention, the foldable element material has a Young's modulus at ambient use temperatures (e.g., 25° C.) that is higher than the Young's modulus of the expandable element material. The Young's modulus (also sometimes referred to as the modulus of elasticity or elastic modulus) of a material is a measure of the stiffness of a material and is the ratio of the linear stress to the linear strain. The expandable element material may have a low to medium shore A hardness, e.g., about 1 to about 30. The foldable element material typically has a higher shore A hardness, e.g., about 70 to about 100.

Examples of polymers suitable for use in the foldable element material include, but are not limited to, polyurethanes (including the polyurethanes sold under the brand name "Pellethane" by Microspec and Lubrizol), nitrile rubbers (including the acrylonitrile methylacrylate copolymer-grafted nitrile rubbers sold under the brand name "Barex" by Ineos), polyvinylidene chlorides, and the like.

Examples of polymers suitable for use in the expandable element material include, but are not limited to, elastomeric polysiloxanes (i.e., silicone elastomers, including for example the silicone elastomers sold under the brand name "Silastic" by Dow Corning and under the brand name "Elastosil" by Wacker Chemie), thermoplastic elastomers (e.g., EPM and EPDM), thermoplastic olefin elastomers (TPOs), thermoplastic vulcanizates (TPVs), thermoplastic polyurethanes (TPUs), fluoroelastomers, and the like.

In addition to the above-mentioned criteria, the material used to construct the foldable element material generally should be selected to be compatible with the medium 122 to be used in the occlusion element. In particular, since the medium 122 will typically be in contact with the inner surface of the foldable element 118, it will be desirable to utilize a material for the foldable element 118 that is not degraded by the medium 122 and is highly impermeable to the medium 122 so as to minimize loss of the medium 122 through the foldable element 118. To decrease the permeability of the foldable element material, a barrier layer may comprise part of the material. For example, a coextruded multilayer film containing a central layer of polyvinylidene chloride sandwiched between outer layers of polyolefin (such as the films sold under the brand name "Saranex" by Dow Chemical) may be utilized. A biaxially-oriented polyethylene terephthalate film which has been metallized can also be used to coat another film material such as a polyurethane in order to reduce its permeability towards the medium 122. A nanocomposite coating, such as those offered by InMat, Inc., may also be used to improve the barrier properties of the foldable element material.

The medium 122 utilized in the occlusion device may be any suitable liquid, gas or gel capable of filling the space between the insertion element 116 and the foldable element 118, causing the foldable element 118 to press outwardly against the expandable element 120 such that the outer surface of the expandable element 120 comes into contact with the inner surface of a user's ear canal wall 106. The medium 122 should be capable of maintaining a comfortable level of pressure for the user of the earpiece device 110. As mentioned above, the medium 122 and the material used to form the foldable element 118 should be selected for compatibility. The following additional criteria may be taken into account in choosing the substance or mixture of substances to be used as the medium 122:

1). Relatively low viscosity, e.g., less than 5 cS at 25° C. A suitably low viscosity may improve the fluid flow rate achievable between fluid reservoirs.

2). High vapor pressure, e.g., at least 1 mm Hg at 25° C. A relatively high vapor pressure facilitates complete and rapid evaporation of the medium 122 in the case of rupture of the foldable element 118 and expandable element 120 or other leakage from the earpiece device 110.

3). Low chemical reactivity (e.g., reactivity according to NFPA and HMIS classification of 0).

4). Low flammability (e.g., a flashpoint above 75° C.; flammability HMIS and NFPA classification of not more than 2).

5). Little or no biological and environmental toxicity (e.g., Health HMIS classification not greater than 1).

6). Low water solubility, to prevent or reduce corrosion and freezing of mechanical components (e.g., less than 50 ppm solubility in water).

7). Low pour point (e.g., <−40° C.), to ensure consistent operation regardless of temperature and to prevent device damage due to frozen solids.

8). Low ozone depletion potential (e.g., ODP=0).

9). Low specific heat (e.g., <1 calorie/gram° C.), so that the earpiece device 110 is capable of reaching body temperature faster, thereby resulting in improved user comfort.

10). Low thermal conductivity (e.g., <0.075 W/m-K), to improve user comfort when the medium temperature is different from body temperature.

11). Low viscosity/temperature coefficient (e.g., <0.75), to provide consistent operation regardless of the temperature of the medium 122.

12). Low surface tension (e.g., <25 mN/m), to aid in the evaporation of the medium 122 in the event of medium leakage from the earpiece device 110 and to improve valve operation.

13). Low thermal expansion (e.g., <0.0025 K.sup.-1), also to ensure consistent operation regardless of temperature.

14). Boiling point of at least 75° C. to ensure that the earpiece device 110 will not be damaged by volume or pressure changes due to boiling medium 122.

The medium 122 may, for example, be a fluorinated morpholine, a hydrofluoroether, or a liquid siloxane (silicone fluid). Examples of specific substances suitable for use as the medium 122 include, but are not limited to, perfluoro N-alkyl morpholines where the alkyl groups are C1-4 alkyl groups (such as FLUORINERT FC-770, available from 3M), 1,1,1,2,2,3,4,5,5,5-decafluoro-3-methoxy-4-(trifluoromethyl)-pentane (such as NOVEC 7300 engineered fluid, available from 3M), decamethylcyclopentasiloxane (such as XIAMETER PMX-0245, available from Dow Corning), and dedecamethylpentasiloxane (such as XIAMETER PMX-200 2CS, available from Dow Corning).

The insertion element 116 may be formed from, for example, thermoplastic elastomer (TPE) materials, other materials having elastomeric properties (e.g., silicone), or other malleable, flexible material capable of conforming to the ear canal 104. The foldable element 118 and the expandable element 120 may be attached to the insertion element 116 via any suitable attachment method, such as, but not limited to, bonding, adherence with an adhesive, thermal bonding, heat welding, heat sealing, molding and ultrasonic bonding. A mechanical element such as an elastic band or metal clip could alternatively be used to hold the foldable element 118 in place against the outer surface of the insertion element 116. The attachment method should form a complete seal around the perimeter of the insertion element 116 at the interfaces between the foldable element 118 and the insertion element 116, to avoid leakage or loss of the medium 122 through such interface. The expandable element 120 may be attached to the outer surface of insertion element 116 at the same locations as the foldable element 118. Alternatively, attachment of these elements may be accomplished at different locations along the length of the insertion element 116, provided that the foldable element 118 remains enclosed within the expandable element 120. The insertion element 116 should be configured such that it is capable of being readily inserted into the ear canal 104 of a user. Typically, it is elongated in shape and may take, for example, the form of a cylindrical tube having a diameter of from 1.5 to 3 mm. To facilitate insertion of the occlusion section 112, it is also desirable that the overall maximum diameter of the occlusion section 112 (when little or no medium 122 has been introduced between the insertion element 116 and the foldable element 118) be selected to be less than the minimum diameter of the ear canal 104.

As discussed above, the acoustic attenuation provided by occlusion section 112 may depend upon the state of foldable element 118. Thus, the acoustic attenuation of occlusion section 112 may be determined largely by the physical characteristics of expandable element 120 alone (when foldable element 118 is not completely unfolded and the outer periphery of expandable element 120 initially contacts ear canal wall 106, as shown in FIG. 3B), and by the physical characteristics of foldable element 118 alone (when foldable element 118 is completely unfolded, as shown in FIG. 3C). Therefore, as discussed above, the amount of medium 122 (presented between insertion element 116 and foldable element 118) may be varied to adjust the transmission loss provided by occlusion section 112.

The selection of physical parameters of occlusion section 112 (FIG. 1) to provide predetermined sound attenuation characteristics is described below, through acoustical modeling. It is often possible and convenient to represent an acoustical system with a lumped element model, as an acoustical circuit analogous to an electrical circuit. For example, an acoustical system may be represented as an acoustic impedance (or acoustic mobility). In acoustic impedance analogs, for example, the sound pressure and volume velocity correspond to voltage and current, respectively. For example, occlusion section 112 (FIG. 1) in ear canal 104 may be modeled by an acoustical impedance circuit. A lumped-element circuit is described below with circuit elements, such as acoustic resistances and capacitances, representing various aspects of the physical system.

As described further below with respect to FIG. 4A-FIG. 9, physical parameters of occlusion section 112 may be selected to provide a predetermined sound attenuation characteristic over a frequency band. For example, a compliance of expandable element 120, the type of medium 122 and the state of foldable element 118 (via the amount of medium 122 used to unfold foldable element 118) may be used to design occlusion section 112 with a specific sound attenuation characteristic (such as a high pass filter, a band pass filter or a low pass filter).

Figure 4A:
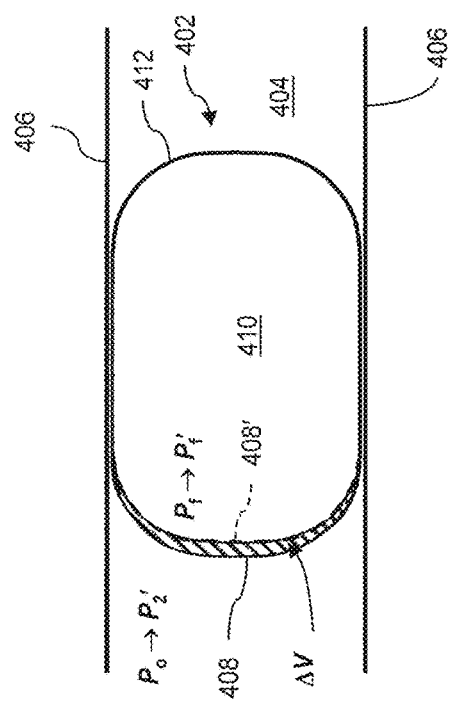
FIG. 4A is a cross section diagram of an exemplary balloon in a tube illustrating a change in static pressure, according to an embodiment of the present invention.
Figure 4B:
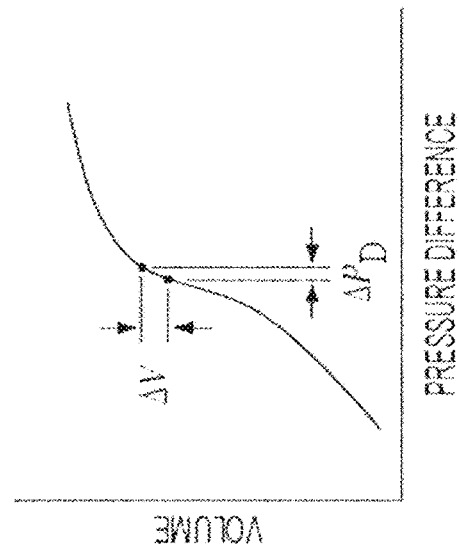
FIG. 4B is a graph of volume as a function of pressure difference for the balloon shown in FIG. 4A.
Figure 4C:
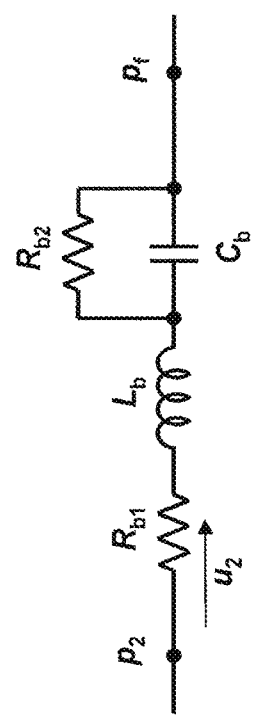
FIG. 4C is an electro-acoustical circuit diagram representing a face of the balloon shown in FIG. 4A, according to an embodiment of the present invention.

Referring to FIGS. 4A, 4B and 4C, an equivalent acoustical element representation of one face of balloon 402 filled with medium 410 to a volume V in tube 404 is described. In particular, FIG. 4A is a cross section diagram of balloon 402 in tube 404; FIG. 4B is an example of a volume of one face of balloon 402 (for example, face 408) with pressure difference; and FIG. 4C is an electro-acoustical circuit diagram representing a face of the balloon shown in FIG. 4A.

In the acoustical element representations described with respect to FIG. 4A-FIG. 5C, balloon 402 may represent foldable element 116 (when foldable element 116 is completely unfolded and the outer periphery of expandable element 120 initially contacts ear canal wall 106, as shown in FIG. 3B) or expandable element 120 (when foldable element 116 is not completely unfolded, as shown in FIG. 3C). Thus, the material of balloon 402 may be selected to represent foldable element 116 or expandable element 120, depending on the current folding state (i.e., partially unfolded or completely unfolded) of foldable element 116 (which in turn depends on the amount of medium 410 used to unfold foldable element 116).

Balloon 402 and medium 410 may each be represented as acoustical elements. Because balloon 402 is within tube 404, the band of balloon material in contact with tube walls 406 does not move. This effectively separates balloon 402 into two parts, upstream face 408 and downstream face 412. It is understood that the acoustical element representation of downstream face 412 is the same as that of upstream face 408. Thus, only upstream face 408 is considered below.

The static interior pressure of balloon 402 is $P_f$ and the outside pressure on either side of the balloon 402 is the ambient atmospheric pressure $P_o$, giving a pressure difference $P_D = P_f - P_o$. If the outside pressure is changed to $P_2'$, there will be a change in the static equilibrium of the balloon 402. Face 408 of balloon 402 moves to a new position and may have a different shape (represented as face 408'), sweeping out a volume $\Delta V$. Thus, the interior pressure will change to a new value $P_f'$, giving a new difference in pressure across the material $P_D' = P_f' - P_2'$.

Although, in general, the relationship between the change in pressures and the volume of balloon 402 may be complicated, for the acoustical behavior, it is assumed that these changes are very small, so that a simple acoustical representation of balloon 402 may be determined.

FIG. 4B illustrates an example of the volume change of face 408 of balloon 402 with a change in pressure difference across the material. Over a small change in pressure difference $\Delta P_D = P_D' - P_D$, the curve is very nearly linear and the volume change $\Delta V$ may be represented as:

$$\Delta V \approx \left(\frac{\partial V}{\partial P_D}\right)_{P_D} \Delta P_D \equiv C_b \Delta P_D$$

where a constant of proportionality $C_b$ has been introduced.

For acoustic pressures, the pressures acting on face 408 may be considered to oscillate sinusoidally at some angular frequency ($\omega$) in time about their static values, and may be represented by complex notation as:

$$\begin{aligned} P_2' &= P_o + \text{Re}\{p_2 e^{i\omega t}\} \\ P_f' &= P_f + \text{Re}\{p_1 e^{i\omega t}\} \end{aligned}$$

where $p_f$ and $p_2$ are the (complex) sound pressures on either side of the balloon face, so that $$\Delta P_D = \text{Re}\{(p_f - p_2)e^{i\omega t}\}$$

Similarly, the volume changes harmonically as $$\Delta V = \text{Re}\{V^* e^{i\omega t}\}$$

where V is the static volume enclosed by face 408 of balloon 402. Thus, the volume velocity U (i.e., the rate of volume flow with time) may be represented as $$U \equiv \text{Re}\{u_2 e^{i\omega t}\} = -\frac{d\Delta V}{dt} = -\text{Re}\{i\omega V^* e^{i\omega t}\}$$

According, the sound pressure difference is related to the complex volume velocity $u_2$, as $$P_2 - P_f = \frac{u_2}{i\omega C_b}$$

Thus, one side (for example face 408) of balloon 402 behaves as an acoustical capacitance $C_b$. The value of the capacitance $C_b$ is given by the slope of the tangent line in FIG. 4B.

The above analysis, being based on static deformations of the balloon, neglects two other contributions. Namely, mass loading of the balloon material and internal dissipation mechanisms. The mass of the material forming face 408 of the balloon 402 has an acceleration a given by $$\rho_b d a \approx -\Delta P_D + \Delta P_{\it eff}$$

where $\rho_b$ is the density of the balloon material, d is the thickness of the balloon material and $\Delta P_{\it eff}$ is the effective pressure difference due to the viscous and elastic properties of the balloon material. For viscoelastic materials, there are several modeling approaches that can used to incorporate dissipation.

According to one approach, the viscous damping is assumed to act like a dashpot in mechanical series with a spring (i.e., the elastic restoring force). The change of volume is comprised of two contributions, namely:

$$\Delta V = \Delta V_e + \Delta V_v$$

where the elastic contribution is $$\Delta P_{\it eff} = \Delta V_e / C_b$$

and the viscous contribution is $$\Delta P_{\it eff} = R_b \frac{d\Delta V_V}{dt}$$

Complex notation can be introduced to obtain:

$$P_2 = P_f + i\omega L_b u_2 + \frac{u_2}{i\omega C_b + 1/R_b}$$

where the inductance $L_b$ is given by $$L_b \approx \frac{\rho_b d}{A_o}$$

and $A_o$ is the internal cross sectional area of the enclosing tube 404.

According to another approach, the balloon material is assumed to behave like a dashpot in parallel with a spring. The effective pressure difference may be represented as the sum $$\Delta P_{\it eff} = \Delta P_e + \Delta P_v$$

where the elastic component is $$\Delta P_e = \Delta V / C_b$$

and the viscous component is $$\Delta P_V = R_b \frac{d\Delta V}{dt}$$

Complex notation can be introduced to the above equations to obtain:

$$P_2 = P_f + R_{b1} + i\omega L_b u_2 + \frac{u_2}{i\omega C_b}$$

Both models, i.e., Eq. (11) or Eq. (16), can be applicable for various materials over a limited range of frequencies. Eqs. (11) and (16) may be merged to produce:

$$P_2 = P_f + R_{b1} + i\omega L_b u_2 + \frac{u_2}{i\omega C_b + 1/R_{b2}}$$

Based on Eq. (17), one face (for example face 408) of balloon 402 may be represented as an equivalent electro-acoustical circuit (i.e., an acoustical impedance analog), as shown in FIG. 4C. As discussed above, the other face (for example, face 412) of the balloon 402 will behave in a similar fashion, with the same lumped-elements being applicable.

Figure 5A:
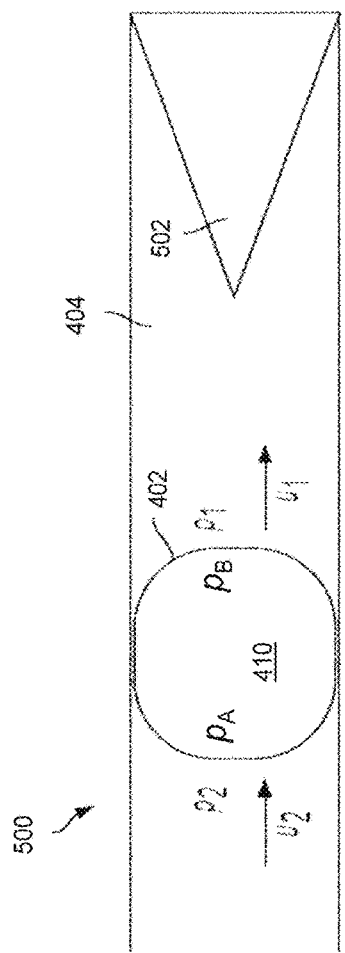
FIG. 5A is a cross section diagram of an exemplary acoustical system, according to an embodiment of the present invention.
Figure 5B:
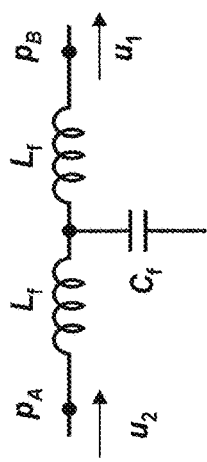
FIG. 5B is a an electro-acoustical circuit diagram representing an interior of the balloon of the acoustical system shown in FIG. 4A.
Figure 5C:
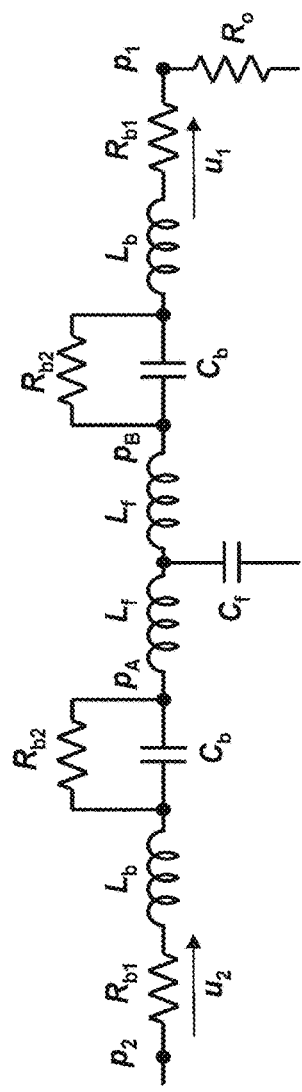
FIG. 5C is an electro-acoustical circuit diagram representing the acoustical system shown in FIG. 4A.

Referring to FIGS. 5A, 5B and 5C, acoustical system 500 representing an occlusion section in an ear canal is shown. In particular, FIG. 5A is a cross section diagram of acoustical system 500 including balloon 402 in tube 404 having anechoic termination 502; FIG. 5B is an electro-acoustical circuit diagram of an interior of medium-filled balloon 402; and FIG. 6B is an electro-acoustical circuit diagram of acoustical system 500.

Acoustical system 500 represents an expandable element or a foldable element (balloon 402) in an ear canal (tube 404) having a tympanic membrane (anechoic termination 502). Although not illustrated, balloon 402 may be formed on an insertion element (such as insertion element 116 shown in FIG. 1).

Referring to FIG. 5A, the pressure just inside the one side of the balloon 402 is $p_A$ and the pressure just inside the opposite side of balloon 402 is $p_B$. In FIG. 5A, medium 410 may include, for example, a gas or a liquid (referred to herein as fluid 410). Sound pressures and volume velocities are related through a transfer matrix T by $$\begin{bmatrix} P_A \\ u_2 \end{bmatrix} = T \begin{bmatrix} P_B \\ u_1 \end{bmatrix} = \begin{bmatrix} \cos k_f \ell & Z_f \sin k_f \ell \\ z_f^{-1} \sin k_f \ell & \cos k_f \ell \end{bmatrix} \begin{bmatrix} P_B \\ u_1 \end{bmatrix}$$

where l represents the effective length of the balloon 402, $\rho_f$ represents the fluid density of fluid 410, $c_f$ represents the speed of sound in fluid 410, $k_f = \omega/c_f$ represents the wavenumber and $Z_f$ represents the characteristic impedance of the fluid 410. The characteristic impedance $Z_f$ may be represented as $$Z_f = \frac{\rho_f c_f}{A_o}$$

In Eq. (18), the argument $k_f l$ is typically small for balloons whether filled with air or liquid. The matrix equations (Eq. (18)) may be approximated by a T-network. For example, the interior of balloon 402 may be represented as an equivalent electro-acoustical circuit, as shown in FIG. 5B. In FIG. 5B, the lumped elements may be defined as $$L_f = \frac{\rho_f \ell}{A_o}$$

$$C_f = \frac{A_o \ell}{\rho_f c_f^2}$$

In acoustical system 500, the anechoic termination 502 for the tube 404 may be represented by the characteristic resistance of the tube 404, as $$R_o = \frac{\rho_o c_o}{A_o}$$

where $\rho_o$ and $c_o$ are the density and sound speed of air, respectively.

Based on the acoustical elements representing faces 408, 412 (FIGS. 4A and 4C) 412, an interior of balloon 402 (i.e., fluid 410) (FIG. 5B) and tube 404, acoustical system 500 may be represented as an equivalent electro-acoustical circuit, as shown in FIG. 5C. It is understood that the electro-acoustical circuit may be modified to account for the finite size of insertion element 116 (FIG. 1) on which balloon 402 may be mounted.

Network methods may be applied to calculate various quantities of the acoustical elements if values for the various circuit elements are available. Once parameter values have been assigned to the various circuit elements, the sound pressures and volume velocities may be calculated using standard circuit analysis. For example, the attenuation of sound as it passes through the acoustical system 500 may be determined as:

$$\Delta L = 20 \log \left| \frac{P_1}{P_2} \right|$$

Capacitance $C_b$ corresponding to each face of balloon 402 may be determined, for example, based on a model of the inflation dynamics of balloon materials, as described further below.

Figure 6:
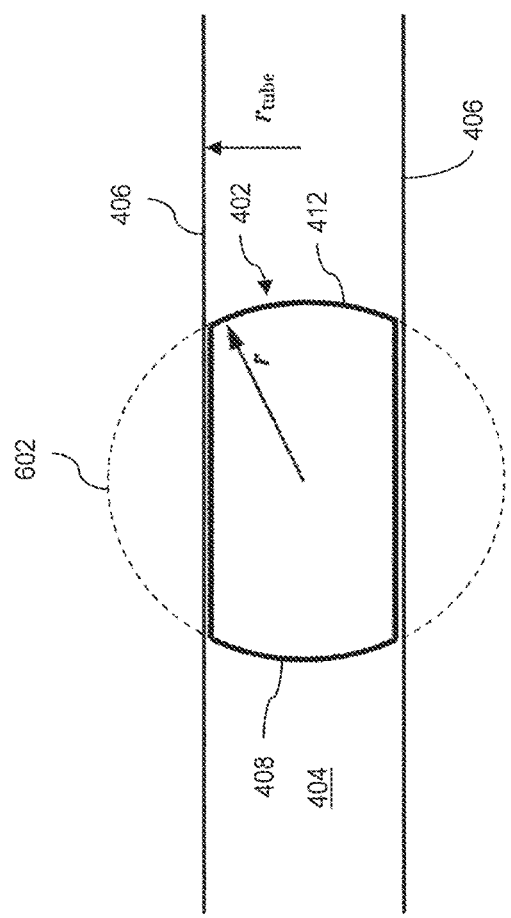
FIG. 6 is a cross section diagram of an exemplary balloon in a bounding tube illustrating a dependence of the inflation geometry on the bounding tube, according to an embodiment of the present invention.

Referring to FIG. 6, a cross section diagram of balloon 402 in tube 404 is shown. If balloon 402 were not constrained by tube 404 (i.e., a bounding tube) having radius $r_{tube}$, balloon 402 would be capable of expanding to form spherical-shaped balloon 602 having radius r. For expansion of balloon 402 within bounding tube 404, it may be assumed that balloon 402 still takes on an approximately spherical shape within the bounding tube, at least at faces 408, 412, as shown in FIG. 6. Moreover, it may be assumed that the stretching of the balloon material at each face 408, 412 of balloon 402 is the same as if balloon 402 expands without tube 404 being present.

On inflation, from static pressure $P_o$ to $P_f$, balloon 402 expands from a radius of $r_o$ to a radius r. Balloon 402 also undergoes a thinning of the balloon material from $d_o$ to d.

Two different types of balloon materials are discussed below. The first type relates to relatively stiff balloon materials, such as polyurethane, with the initial radius $r_o$ greater than the radius $r_{tube}$ of the bounding tube 404 (such as foldable element 118 as shown in FIG. 1). The second type relates to compliant balloon materials, such as silicone rubber, with its initial radius less than the radius $r_{tube}$ of the bounding tube 404 (such as expandable element 120 as shown in FIG. 1).

For a relatively stiff material with initial radius $r_o$ greater than the radius $r_{tube}$ of the bounding tube 404, the tension T in the spherical balloon material is related to the pressure difference $P_D$ as:

$$T = rP_D/2$$

and the stress may be represented as $$\frac{Tr}{d_o r_o} = \frac{r^2 P_D}{2 d_o r_o}$$

The strain may be represented as $$\frac{r - r_o}{r_o}$$

The stress and strain are related by the Young's modulus E, such that $$\frac{r^2 P_D}{2 d_o r_o} = E \frac{r - r_o}{r_o}$$

leading to $$P_D = \frac{2 d_o E (r - r_o)}{r^2}$$

Furthermore, the inflation volume of balloon 402 may be represented as $$V \approx 2 r A_o$$

For a relatively stiff material, the initial and final balloon radii will be similar, i.e., $r \approx r_o$. Thus, Eq. (27) may be represented as $$P_D \approx \frac{2 d_o E (r - r_o)}{r_o^2}$$

To apply Eq. (1), it is assumed that there are very small changes of radius due to acoustic excitation. Thus, $$\delta P_D \approx \frac{2 d_o E}{r_o^2} \delta r$$

The volume swept out by the change $\delta r$ may be represented as $$\delta V \approx A_o \delta r$$

The effective capacitance $C_b$ may thus be represented as $$C_b \approx \frac{r_o^2 A_o}{2 d_o E}$$

Given Eq. (32) for capacitance $C_b$ (for relatively stiff materials), the electro-acoustical circuit shown in FIG. 5C may be evaluated and its attenuation performance determined.

For example, a relatively stiff material such as polyurethane may include a Young's modulus of about $25 \times 10^6$ Pa. For a sample calculation of the effective capacitance $C_b$ for a polyurethane balloon, it is assumed that an initial balloon radius $r_o$ is 5 mm, an initial material thickness $d_o$ is 0.04 mm, and an internal tube area $A_o$ is $7.1256 \times 10^{-5}$ mm$^2$. The capacitance $C_b$ may be determined from Eq. (32) for this example as $8.9 \times 10^{-13}$ m$^3$/Pa.

Figure 7A:
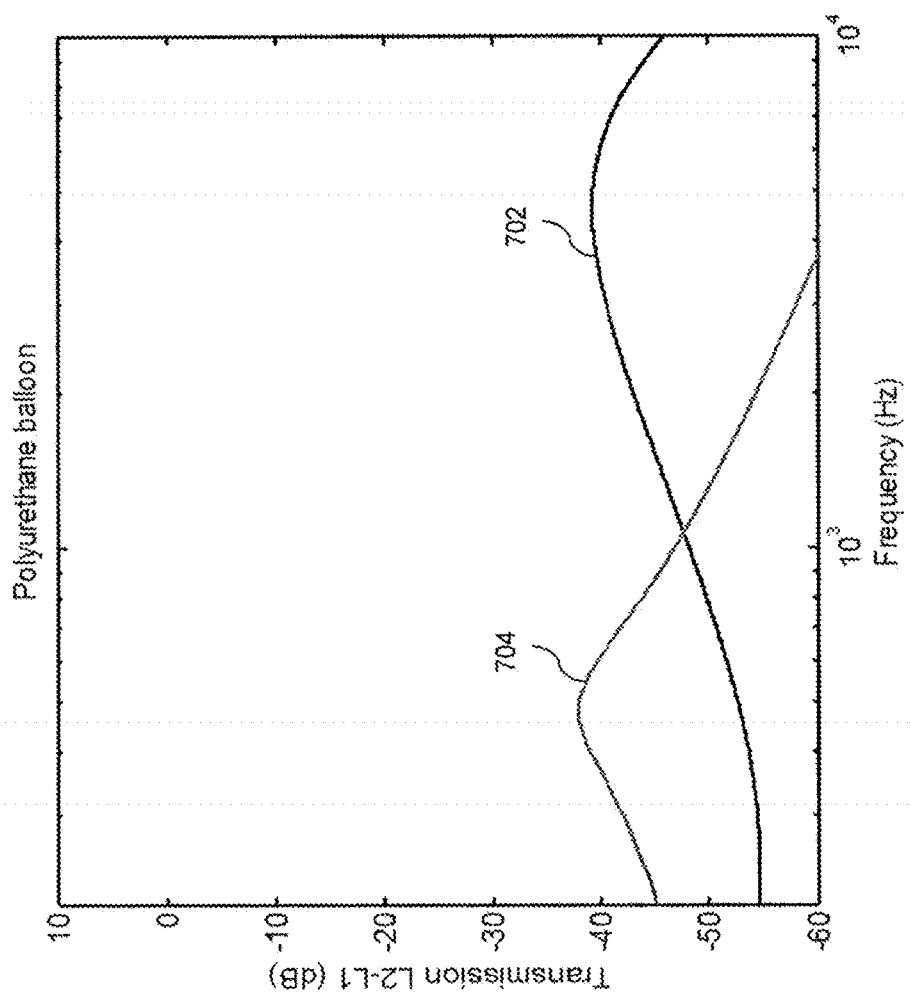
FIG. 7A is a graph of transmission loss as a function of frequency for the electro-acoustical circuit shown in FIG. 5C, for various mediums with an expandable element formed of polyurethane, according to an embodiment of the present invention.
Figure 7B:
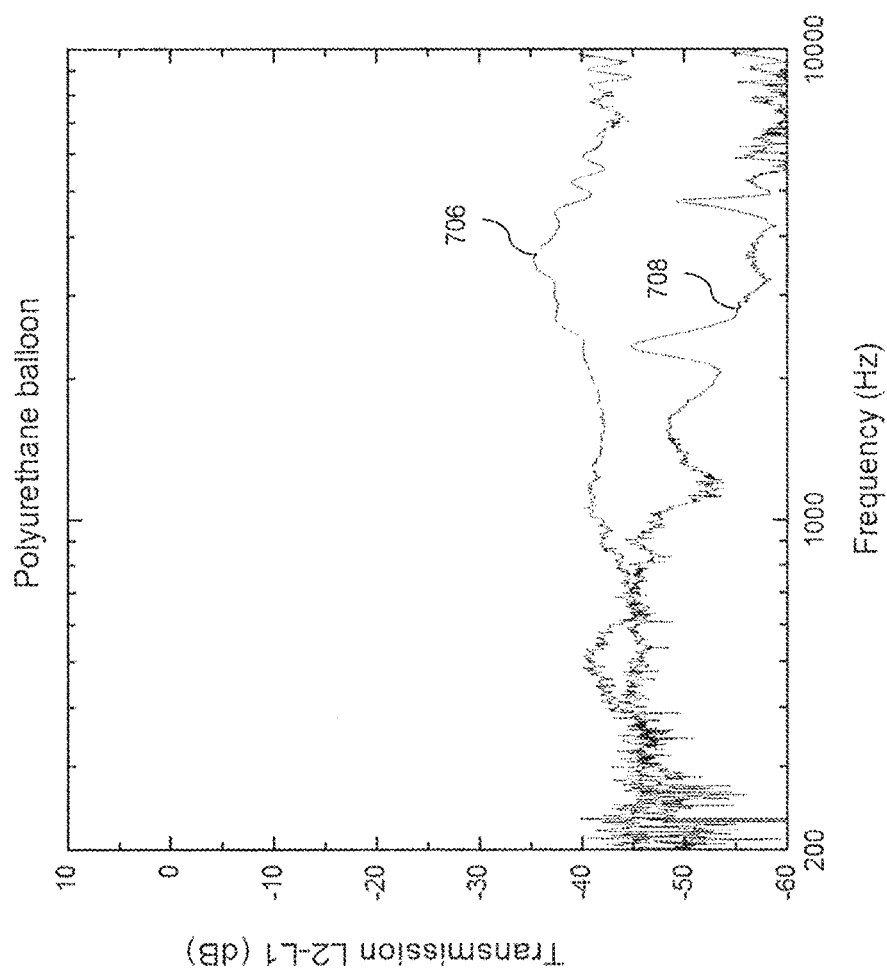
FIG. 7B is a graph of transmission loss as a function of frequency for the acoustical system shown in FIG. 5A, for various mediums with an expandable element formed of polyurethane, according to an embodiment of the present invention.

Referring to FIGS. 7A and 7B, the attenuation performance for a polyurethane balloon for the above example is shown. In particular, FIG. 7A is a graph of transmission loss as a function of frequency as determined for the electro-acoustical circuit shown in FIG. 5C; and FIG. 7B is a graph of transmission loss as a function of frequency as measured for the acoustical system shown in FIG. 5A.

In FIG. 7A, the attenuation performance for the electro-acoustical circuit is analyzed for a polyurethane balloon filed with air (curve 702) and for a polyurethane balloon filled with a liquid (FC-770) (curve 704). In both cases, a transmission loss of about 40 dB or more is provided over a broad range of frequencies.

For the results shown in curve 702 of FIG. 7A, it is assumed that a density of air is 1.2 kg/m$^3$ and a sound speed of air is 343 m/s. For curve 704, it is assumed that a density of FC-770 is 1793 km/m$^3$ and a sound speed of FC-770 is 1300 m/s. For curves 702 and 704, it is assumed that the density of polyurethane is 1200 kg/m$^3$. Some damping is also introduced by assigning values of $5 \times 10^7$ and $7 \times 10^8$ to $R_{b1}$ and $R_{b2}$, respectively (see FIG. 5C).

For comparison, the measured transmission loss on an actual balloon of polyurethane is shown in FIG. 7B. In FIG. 7B, curve 706 corresponds to a balloon filled with air and curve 708 corresponds to a balloon filed with FC-770. The polyurethane balloon has a thickness of 0.04 mm, uninflated. The measured results in FIG. 7B are in agreement with the transmission loss predicted in FIG. 7A.

The results shown in FIGS. 7A and 7B are for relatively stiff materials with an initial radius greater than the radius of the bounding tube 404 (FIG. 6) (such as foldable element 118 shown in FIG. 1).

Next, the capacitance $C_b$ is determined for compliant materials such as silicone rubber having an uninflated radius that is smaller than radius of the bounding tube 404 (FIG. 6) (such as expandable element 120 shown in FIG. 1). On inflation, this type of balloon material stretches much more than would a less-compliant material (such as polyurethane). For example, elongations of 600% or more may be anticipated. The capacitance $C_b$ of compliant materials may be determined, for example, by modeling the balloon material as a Mooney-Rivlin type of material.

For example, the expansion of a spherical balloon made of a rubber-like material may be represented as $$P_D = \frac{2 s_1 d_o}{r_o} \left[ \frac{r_o}{r} - \left(\frac{r_o}{r}\right)^7 \right] \times \left[ 1 - \frac{S_{-1}}{S_1} \left(\frac{r}{r_o}\right)^2 \right]$$

where $s_1$ and $s_{-1}$ are the Mooney-Rivlin parameters. Any change in the pressure difference may be accompanied by a change in the inflated radius. Eq. (33) may be differentiated, forming $$\delta P_D = \frac{2 s_1 d_o}{r_o} \left[ -\frac{S_{-1}}{S_1} - 5 \frac{S_{-1}}{S_1} \left(\frac{r_o}{r}\right)^6 - \left(\frac{r_o}{r}\right)^2 + 7 \left(\frac{r_o}{r}\right)^2 \right] \delta r$$

Based on Eqs. (1), (31), and (34), the effective capacitance $C_b$ may be determined as $$C_b = \frac{A_o r_o}{2 s_1 d_o}\left[-\frac{S_{-1}}{S_1} - 5\frac{S_{-1}}{S_1}\left(\frac{r_o}{r}\right)^6 - \left(\frac{r_o}{r}\right)^2 + 7\left(\frac{r_o}{r}\right)^8\right]^{-1}$$

Eq. (35) may be simplified, by assuming that the balloon 402 (FIG. 6) is being inflated to a considerable extent, so the limiting behavior with $r \gg r_o$ is obtained. Accordingly, Eq. (35) may be represented as $$C_b \approx \frac{A_o r_o^2}{2 s_{-1} d_o}$$

Thus, given Eq. (36) for capacitance $C_b$ (for compliant materials), the electro-acoustical circuit shown in FIG. 5C may be evaluated and its attenuation performance determined.

For example, silicone rubber can be represented by various values, reflecting the broad variations in material properties. For a sample calculation of the effective capacitance $C_b$ for a silicone rubber balloon, a value of 100 kPa for the parameter $s_{-1}$ is selected, and it is assumed that an initial effective radius $r_o$ is 1 mm and an initial material thickness $d_o$ is 0.18 mm. The capacitance $C_b$ may be determined from Eq. (36) for this example as $2 \times 10^{-12}$ m$^3$/Pa.

Figure 8A:
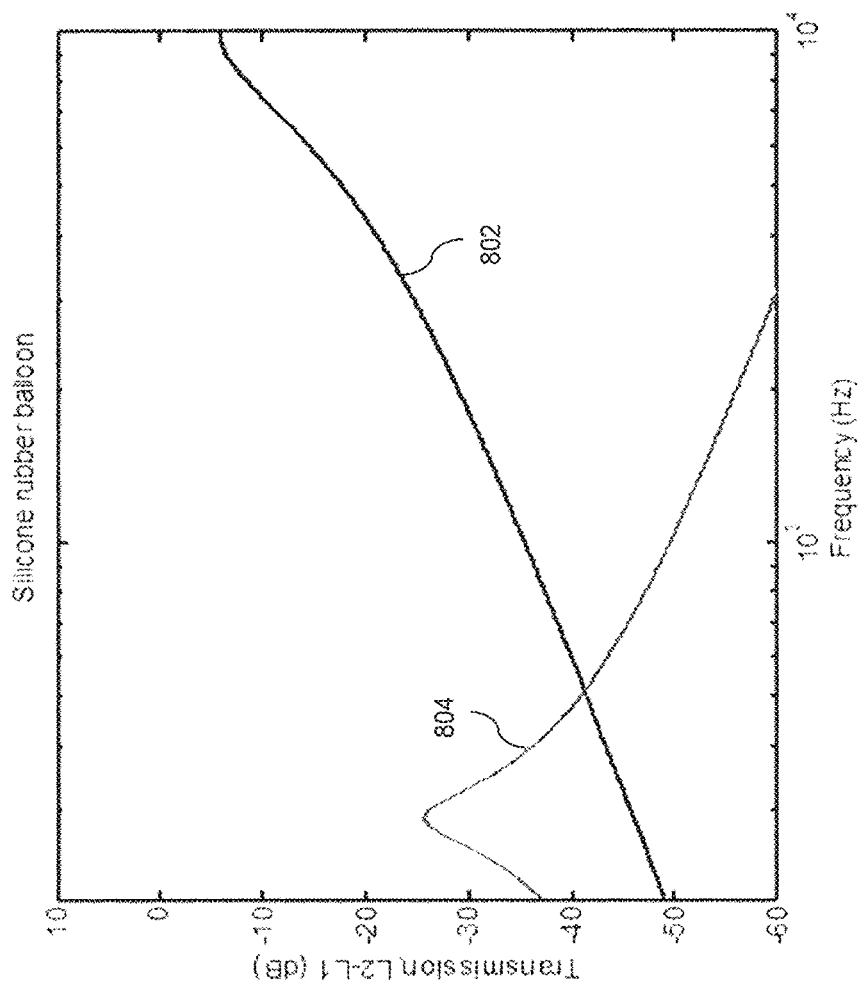
FIG. 8A is a graph of transmission loss as a function of frequency for the electro-acoustical circuit shown in FIG. 5C, for various mediums with an expandable element formed of silicone rubber, according to an embodiment of the present invention.
Figure 8B:
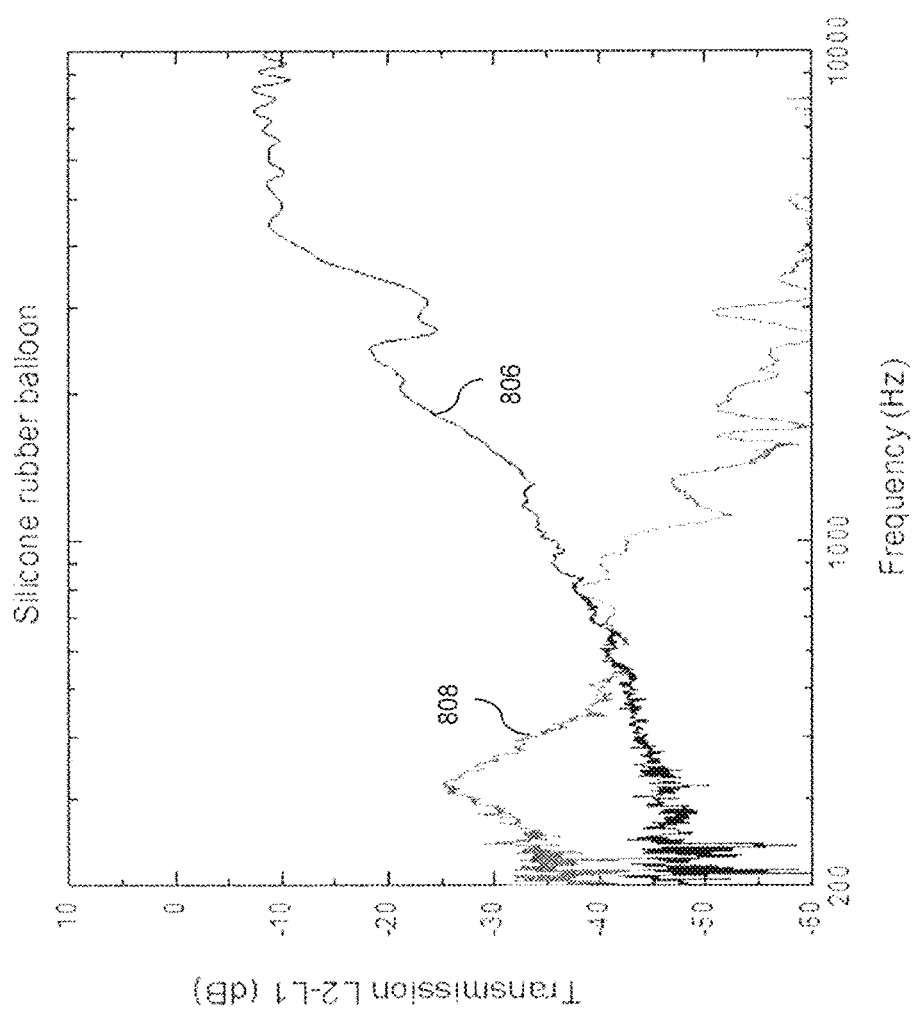
FIG. 8B is a graph of transmission loss as a function of frequency for the acoustical system shown in FIG. 5A, for various mediums with an expandable element of silicone rubber, according to an embodiment of the present invention.

Referring to FIGS. 8A and 8B, the attenuation performance for a silicone rubber balloon for the above example is shown. In particular, FIG. 8A is a graph of transmission loss as a function of frequency as determined for the electro-acoustical circuit shown in FIG. 5C; and FIG. 8B is a graph of transmission loss as a function of frequency as measured for the acoustical system shown in FIG. 5A.

In FIG. 8A, the attenuation performance for the electro-acoustical circuit is analyzed for a silicone rubber balloon filed with air (curve 802) and for a silicone rubber balloon filled with a liquid (FC-770) (curve 804). The calculated acoustical attenuation for a silicone rubber balloon inside a tube of 0.375" inner diameter. The silicone rubber balloon is assumed to be inflated to a radius of 6 mm. It is assumed that the inflation pressure is 300 mbar.

For the results shown in curve 802 of FIG. 8A, it is assumed that a density of air is 1.2 kg/m$^3$ and a sound speed of air is 343 m/s. For curve 804, it is assumed that a density of FC-770 is 1793 km/m$^3$ and a sound speed of FC-770 is 1300 m/s. For curves 802 and 804, it is assumed that the density of silicon rubber is 1100 kg/m$^3$. Some damping is introduced by assigning values of $3 \times 10^6$ and $1.5 \times 10^9$ to $R_{b1}$ and $R_{b2}$, respectively (see FIG. 5C).

For comparison, the measured transmission loss on an actual balloon of silicone rubber is shown in FIG. 8B. In FIG. 8B, curve 806 corresponds to a balloon filled with air and curve 808 corresponds to a balloon filed with FC-770. The balloon that is inflated with air is fabricated using Silastic Q7-4720 Dow-Corning Biomedical Grade ETR elastomer. The balloon that is inflated with FC-770 liquid is fabricated using HT-1001. The thickness of the uninflated balloon material is 0.007" in both cases.

In the discussion above, acoustical system 500 (FIG. 5A) is modeled as including balloon 402, where balloon 402 may represent foldable element 118 (FIG. 1) or expandable element 120 of occlusion section 112. Referring back to FIGS. 3A-3C, the transmission loss (i.e., attenuation char-acteristics) of occlusion section 112 is in fact a combination of the physical characteristics of foldable element 118 and expandable element 120, as well as the amount of medium 122 presented between insertion element 116 and foldable element 118.

The transmission loss (TL) of occlusion section 112 may be summarized as follows:

$$TL = \begin{cases} 0, & V < V_{min} \\ TL_{expandable}, & V_{min} < V < V_{critical} \\ TL_{foldable}, & V > V_{critical} \end{cases}$$

where $V_{min}$ is the volume at which occlusion section 112 just blocks the bounding tube (i.e., ear canal 104) (shown in FIG. 3B), $V_{critical}$ is the critical volume of foldable element 118 (as shown in FIG. 3C), $TL_{foldable}$ is the transmission loss for foldable element 118 and $TL_{expandable}$ is the transmission loss for expandable element 120. It is understood that, in practice, the transition at $V \approx V_{critical}$ may not be abrupt. Rather, there may be a smooth progression from $TL_{expandable}$ to $TL_{foldable}$ with inflation volume V.

Figure 9:
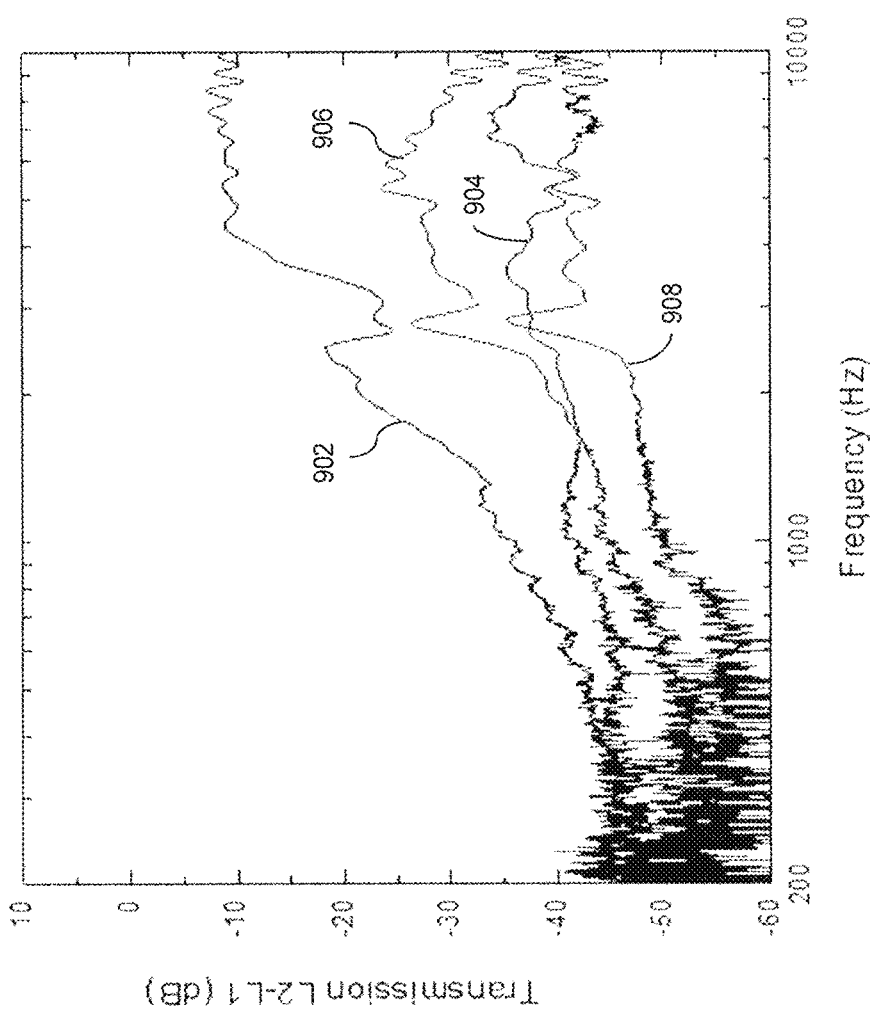
FIG. 9 is a graph of transmission loss as a function of frequency for a balloon (as shown in FIG. 5A) and an occlusion section having a foldable element and an expandable element (as shown in FIG. 1), for various materials, according to an embodiment of the present invention.

Referring next to FIG. 9, a graph of measured transmission loss as a function of frequency is shown for an occlusion section 112 (FIG. 1) having a foldable element 118 and an expandable element 120, according to an embodiment of the present invention. For reference, FIG. 9 also includes the measured transmission loss for a silicone balloon (curve 902) and a polyurethane balloon (curve 904) (i.e., balloon 402 as shown in FIG. 5A). Curves 906 and 908 represent an occlusion section having a polyurethane foldable element and a silicone expandable element. The results shown in curves 906 and 908 are for the foldable element inflated with air at respective internal pressures of 400 mbar and 600 mbar. The results for curves 902 and 904 are for the silicone balloon and the polyurethane balloon inflated with air.

In FIG. 9, the expandable element (for curves 906 and 908) is formed from a silicone rubber sleeve fabricated from Elastosil LR 3003/10 TR A/B. An uninflated thickness of the expandable element is about 0.38 mm. As shown in curve 908, with an internal pressure of 600 mbar, the transmission loss for the occlusion section 112 (FIG. 1) is similar to the polyurethane balloon alone (curve 904). Thus, curve 908 indicates that the critical volume V critical of the polyurethane foldable element is reached (see Eq. (37)). As shown in curve 906, with an internal pressure of 400 mbar, the transmission loss for occlusion section 112 FIG. 1) is between the two reference curves 902 and 904.

Although the invention is illustrated and described herein with reference to specific embodiments, the invention is not intended to be limited to the details shown. Rather, various modifications may be made in the details within the scope and range of equivalents of the claims and without departing from the invention.

I claim:

1. A device for occluding an ear canal, comprising:
   a microphone;
   a speaker; and
   an occlusion section, where the occlusion section comprises:
   an insertion element;
   an acoustic channel, where the speaker is configured to deliver audio content through the acoustic channel;

a foldable element configured to receive a medium, wherein the foldable element is disposed on the insertion element;

an expandable element disposed over the foldable element, wherein the foldable element is configured to unfold upon receiving the medium and the expandable element is configured to expand when the foldable element unfolds, and wherein the foldable element has a different Young's modulus than a Young's modulus of the expandable element.

2. The device of claim 1, further comprising a housing unit including an inflation management system for controlling transfer of the medium.

3. The device of claim 2, wherein the housing unit further comprises a user interface coupled to the inflation management system, wherein the inflation management system is configured to be activated using the user interface.

4. The device of claim 3, wherein, upon activation via the user interface, the inflation management system is configured to fold or unfold the foldable element.

5. The device of claim 1, where the microphone is an ear canal microphone configured to measure a sound pressure level in the ear canal.

6. The device of claim 5, wherein the sound pressure level is utilized by the device to test an integrity of an acoustic seal.

7. The device of claim 1, wherein the expandable element is configured to form an acoustic seal with a portion of an ear canal wall of the ear canal.

8. The device of claim 1, wherein the expandable element comprises a plurality of layers including an inner non-foam layer, an outer foam layer for contact with the ear canal, or a combination thereof.

9. The device of claim 1, further comprising an additional foldable element, wherein the foldable element and the additional foldable element are arranged along a length of the insertion element of the device.

10. The device of claim 1, further comprising a housing unit including a controller, a memory, a battery, a communication unit, or a combination thereof.

11. A method of occluding an ear canal, comprising:
placing an occlusion device within the ear canal, wherein the occlusion device includes:
a microphone;
a speaker; and
an occlusion section, where the occlusion section comprises:
an insertion element;
an acoustic channel, where the speaker is configured to deliver audio content through the acoustic channel;
a foldable element and an expandable element disposed over the folded element, wherein the foldable element is configured to receive a medium; and introducing the medium into the foldable element thereby causing the folded element to unfold and cause the expandable element to expand to contact the ear canal; and wherein the foldable element has a different Young's modulus than a Young's modulus of the expandable element.

12. The method of claim 11, further comprising introducing the medium into the foldable element by introducing the medium into a space between the insertion element of the occlusion device and the foldable element.

13. The method of claim 11, further comprising:
positioning a housing unit of the occlusion device outside the ear canal.

14. The method of claim 11, further comprising:
inserting the expandable element into the ear canal while in a contracted state.

15. The method of claim 11, further comprising:
adjusting a sound attenuation characteristic associated with the occlusion device based on an amount of the medium introduced into the foldable element.

16. The method of claim 11, further comprising:
facilitating communication with a device remote to the occlusion device.

17. The method of claim 11, further comprising:
forming a balloon using the expandable element and the foldable element.

18. The method of claim 11, further comprising:
introducing the medium into the foldable element by transferring the medium from an inflation management system of the occlusion device via a pneumatic channel.

19. A device, comprising:
a microphone;
a speaker;
a communication unit configured to communicate with a device remote from the device; and
an occlusion section, where the occlusion section comprises:
an insertion element;
an acoustic channel, where the speaker is configured to deliver audio content through the acoustic channel;
a foldable element configured to receive a medium;
an expandable element disposed over the foldable element,
wherein the foldable element is configured to unfold upon receiving the medium and the expandable element is configured to expand when the foldable element unfolds, and
wherein the foldable element has a different Young's modulus than a Young's modulus of the expandable element.

* * * * *